United States Patent
Jürgens et al.

(10) Patent No.: US 9,510,735 B2
(45) Date of Patent: Dec. 6, 2016

(54) METHOD AND SYSTEM FOR DISPLAYING VIDEO-ENDOSCOPIC IMAGE DATA OF A VIDEO ENDOSCOPE

(71) Applicant: OLYMPUS WINTER & IBE GMBH, Hamburg (DE)

(72) Inventors: Thorsten Jürgens, Hamburg (DE); Peter Schouwink, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 235 days.

(21) Appl. No.: 14/021,144

(22) Filed: Sep. 9, 2013

(65) Prior Publication Data

US 2014/0012081 A1   Jan. 9, 2014

Related U.S. Application Data

(63) Continuation of application No. PCT/EP2012/000661, filed on Feb. 15, 2012.

(30) Foreign Application Priority Data

Mar. 8, 2011 (DE) .......................... 10 2011 005 259

(51) Int. Cl.
*A61B 1/06* (2006.01)
*A61B 1/04* (2006.01)
(Continued)

(52) U.S. Cl.
CPC ......... *A61B 1/00174* (2013.01); *A61B 1/0005* (2013.01); *A61B 1/00181* (2013.01);
(Continued)

(58) Field of Classification Search
CPC ............ A61B 1/00163; A61B 1/00174; A61B 1/00177; A61B 1/00179; A61B 1/00181; A61B 1/00183; A61B 1/06; A61B 1/0607; A61B 1/0615; A61B 1/0623; A61B 1/0661; A61B 1/00004; A61B 1/00009; A61B 1/00043; A61B 1/00055
(Continued)

(56) References Cited

U.S. PATENT DOCUMENTS 5,995,759 A * 11/1999 Kohayakawa .................. 396/18
6,663,559 B2 * 12/2003 Hale et al. ..................... 600/118
(Continued)

FOREIGN PATENT DOCUMENTS

DE 10 2008 057 734 A1   5/2010
DE 10 2009 020 262 A1   11/2010
(Continued)

OTHER PUBLICATIONS

Japanese Office Action dated Mar. 31, 2015 from related Japanese Patent Application No. 2013-556991, together with an English language translation.
(Continued)

*Primary Examiner* — Thomas J Sweet
*Assistant Examiner* — William Chou
(74) *Attorney, Agent, or Firm* — Scully, Scott, Murphy & Presser, P.C.

(57) ABSTRACT

A method for displaying video-endoscopic image data of a video endoscope having at least one lateral viewing direction, wherein at least one objective which is movable relative to an image sensor about the longitudinal axis of a shaft of the video endoscope and has at least one lateral viewing direction is arranged on the distal end of the shaft of the video endoscope, wherein the viewing direction is changed over from a first viewing direction to a second viewing direction on account of a viewing direction changeover command. Also provided are a video endoscopy system wherein the viewing direction can be changed over from a
(Continued)

first viewing direction to a second viewing direction on account of a viewing direction changeover command and a software program product comprising program code means for carrying out the above method.

9 Claims, 2 Drawing Sheets

(51) Int. Cl.
*A61B 1/00* (2006.01)
*H04N 5/232* (2006.01)
*G02B 23/24* (2006.01)
*H04N 5/225* (2006.01)

(52) U.S. Cl.
CPC ............ *A61B 1/00183* (2013.01); *A61B 1/04* (2013.01); *G02B 23/2484* (2013.01); *H04N 5/23293* (2013.01); *G02B 23/2423* (2013.01); *H04N 2005/2255* (2013.01)

(58) Field of Classification Search
USPC ....... 600/103, 109, 112, 117, 160, 170, 171, 600/173, 175, 176
See application file for complete search history.

(56) References Cited

U.S. PATENT DOCUMENTS

| | | | | |
|---|---|---|---|---|
| 8,668,638 B2* | 3/2014 | Donhowe et al. | ............ | 600/146 |
| 2006/0189842 A1* | 8/2006 | Hoeg et al. | ................... | 600/118 |
| 2006/0206003 A1 | 9/2006 | Hoeg et al. | | |
| 2006/0293565 A1 | 12/2006 | Uchimura et al. | | |
| 2010/0010301 A1* | 1/2010 | Hale | ................. | A61B 1/00096 600/109 |
| 2010/0022838 A1* | 1/2010 | Hoeg | ............................ | 600/131 |
| 2010/0125166 A1 | 5/2010 | Henzler | | |
| 2010/0249507 A1 | 9/2010 | Prisco et al. | | |

FOREIGN PATENT DOCUMENTS

| | | |
|---|---|---|
| EP | 0 347 140 A1 | 12/1989 |
| EP | 0 363 118 A2 | 4/1990 |
| EP | 1 844 696 A1 | 10/2007 |
| EP | 2 147 631 A1 | 1/2010 |
| JP | 3-58401 U | 6/1991 |
| JP | 2005-296063 A | 10/2005 |
| JP | 2007-54511 A | 3/2007 |
| JP | 2007-130132 A | 5/2007 |
| JP | 2007-275257 A | 10/2007 |
| JP | 2009-251574 A | 10/2009 |
| JP | 2009-297419 A | 12/2009 |
| JP | 2009-297421 A | 12/2009 |
| JP | 2010-008483 A | 1/2010 |
| JP | 2010-29658 A | 2/2010 |
| WO | WO0060996 A1 | 10/2000 |
| WO | WO 2008/002830 A2 | 1/2008 |

OTHER PUBLICATIONS

English abstract only of US 2006/293565.
English abstract only of US 2010/022838.
International Search Report dated May 23, 2012 issued in PCT/EP2012/000661.

* cited by examiner

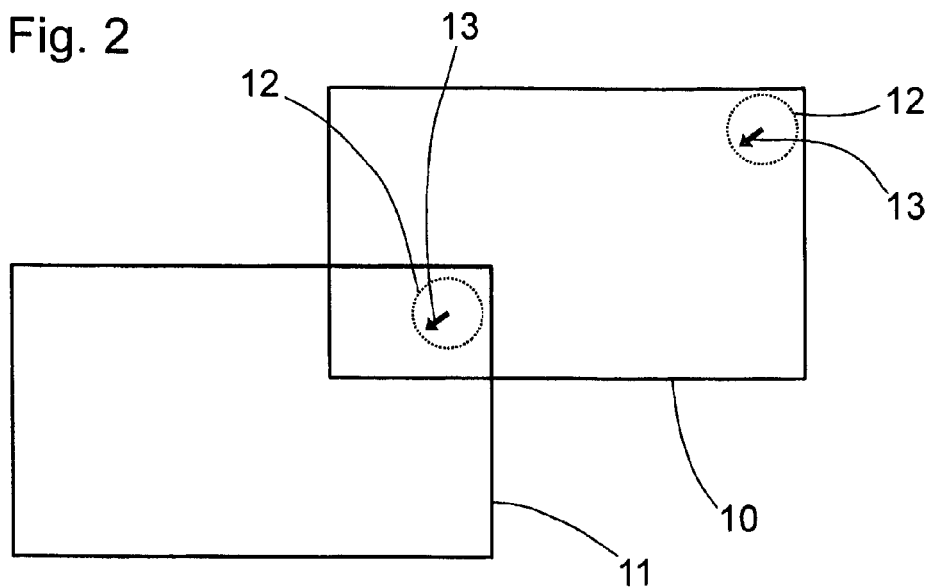
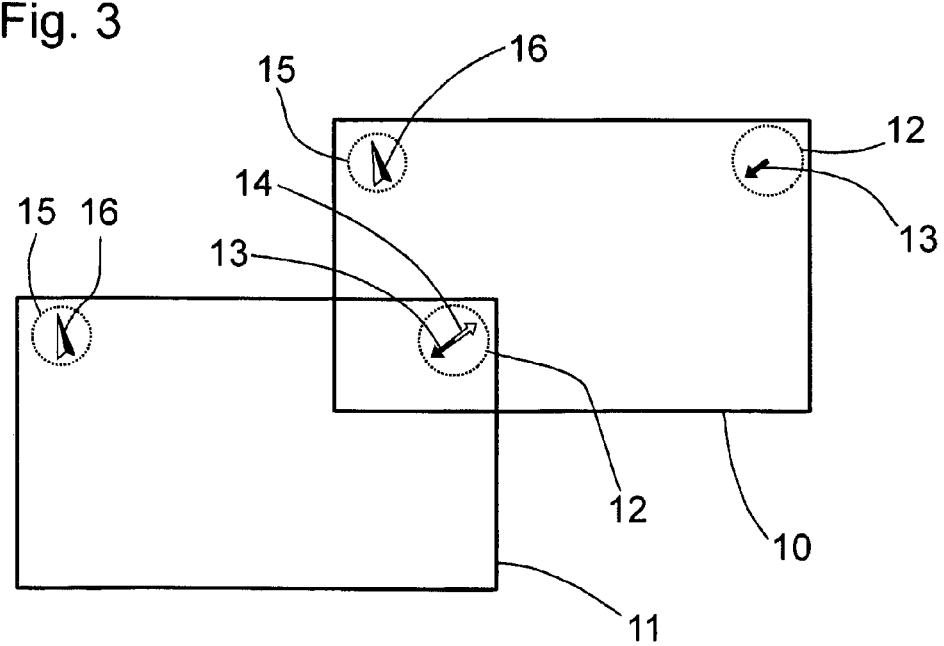

METHOD AND SYSTEM FOR DISPLAYING VIDEO-ENDOSCOPIC IMAGE DATA OF A VIDEO ENDOSCOPE

CROSS-REFERENCE TO RELATED APPLICATION

The present application is a continuation of PCT/EP2012/000661 filed on Feb. 15, 2012, which is based upon and claims the benefit to DE 10 2011 005 259.3 filed on Mar. 8, 2011, the entire contents of each of which are incorporated herein by reference.

BACKGROUND

Field

The invention relates to a method for displaying video endoscopic image data of a video endoscope having at least one lateral viewing direction, wherein at least one objective which is movable relative to an image sensor about the longitudinal axis of a shaft of the video endoscope and has at least one lateral viewing direction is arranged on the distal end of the shaft wherein the viewing direction is changed over from a first viewing direction to a second viewing direction on account of a viewing direction changeover command.

The invention furthermore relates to a video endoscopy system comprising a video endoscope, an image processing unit and an image reproduction device, wherein the video endoscope has an image sensor and at least one objective which is arranged on the distal end of an endoscope shaft and is movable relative to the image sensor about the longitudinal axis of the shaft and has at least one lateral viewing direction, wherein the viewing direction can be changed over from a first viewing direction to a second viewing direction on account of a viewing direction changeover command. Finally, the invention relates to a software program product comprising program code means.

Prior Art

In the scope of the present invention, a video endoscope is understood to be an endoscope in connection with at least one image sensor, which is designed to capture a video recording, independently of whether the image sensor is disposed distally in the endoscope shaft, proximally in a handle, or externally in a camera head, which can be attached to an ocular in the proximal region of the endoscope, thus on the side of a surgeon.

The term image direction, also called "direction of view" (DOV), relates to the lateral image or reverse image deviating from the longitudinal axis of the endoscope and is represented as a polar angle, wherein a viewing angle of 0° means a direct view in the longitudinal direction of the endoscope shaft, while 90°, for example, designates an image direction which deviates at a right angle from the direct view. The present invention relates to endoscopes with which the azimuth angle of the viewing direction, thus the angle of the rotation of the viewing direction about the longitudinal axis of the endoscope, can be changed.

Along with endoscopes having a single lateral viewing objective at the distal end, endoscopes are also known having several objectives which are aligned in discrete viewing directions, and which are designed changeable between the viewing directions. Typical pairs of viewing directions with endoscopes having directions of view which can be changed over, in the sense of the polar angle, for example, 0° and 30°, 0° and 45°, 12° and 70° or 30° and 80°. At least one viewing direction of the pair is therefore a lateral viewing direction. Such objectives having two discrete viewing directions permit the surgeon with a thusly equipped endoscope to be able to view in the different viewing directions as desired. In the scope of the present invention, this adds to the changeability of the azimuth angle of the direction of view.

The present applicant's patent application DE 10 2009 020 262 A1 discloses an endoscope having two viewing directions. The associated objectives are disposed in the distal end region of an endoscope shaft and receive the light coming from their respective field of view, in order to further conduct the light to an image sensor or to an ocular. It is possible to change over between the two viewing directions. A prism is disposed in an intersection of the two optical paths.

The changeover between the viewing directions occurs by removing or introducing a mirror into a gap between the first optical path and the prism. When no mirror is introduced into the gap, the light in the first optical path enters into the prism unimpeded, and through the prism, and arrives at the ocular or at an image sensor. The light of the second optical path is reflected at a first boundary surface of the prism, but in the absence of total reflection, exits at a second boundary surface from the prism in a direction which does not lead to the ocular or to the image sensor. If a mirror is introduced into the gap, the light in the first optical path is blocked, whereas the light of the second optical path is now reflected a second time, and thereby is further conducted laterally to the ocular or to the image sensor.

Additional objectives having two viewing directions are disclosed in the documents EP 0 363 118 B1 and EP 0 347 140 B1.

According to the document EP 0 363 118 B1, for each viewing direction a distal objective part is provided that respectively directs the output optical path in one of two parallel output axes. A proximal objective part can be pivoted together with the image conductor leading further from the objective part through the shaft of the endoscope such that in two pivot locations, the objective part is aligned onto the one or the other of the two output axes.

According to the document EP 0 347 140 B1, an endoscope objective has two distal objective parts for two different viewing directions, and a common proximal objective part. Polarization filters having different fixed polarization units are disposed in the two distal objective parts, and a polarization filter having an adjustable polarization unit is disposed in the proximal objective part. Thus, it is possible to change-over between the two viewing directions. With a simpler design, the image brightness is reduced compared to the other designs.

The document EP 2 147 631 A1 relates to an endoscope having an objective and a swing prism, by means of which the lateral viewing direction is altered.

Furthermore, from the document US 2006/0293565 A1 an endoscope is known comprising an objective that is disposed on a platform in the distal tip of the endoscope, the platform being able to be tipped in one direction or different directions, and is moved by tipping the platform in different directions.

For the orientation thereof in the operative field, which is extremely important with examinations and with surgery, the surgeon depends on his perception of space. It can occur, even with endoscopes having a single lateral viewing direction, that the surgeon in the course of an endoscopic examination or endoscopic procedure loses his orientation after a series of rotations or movements, especially when a part of the endoscope which is important for the orientation, is held by an assistant.

With the mentioned endoscopes comprising viewing directions that can be changed-over there is the fact that the viewing direction is changed-over in discrete steps, so that the displayed objects abruptly change their position. Thus, the challenge for the surgeon is to receive two very different images from one moment to the next that represent different sections of the current operative field. The switching can therefore have a disorienting effect. Because the images are typically displayed on a fixed image screen, moreover the displayed image does not necessarily correspond to the orientation of the endoscope in space and in the operative field.

SUMMARY

The present invention solves the objective to provide a method and a system for displaying video endoscopic image data of a video endoscope having a changeable lateral viewing direction and having a changeable azimuth angle, which allows the orientation of the surgeon in the operative field to be maintained continuously.

This objective is solved by a method for displaying video endoscopic image data of a video endoscope having at least one lateral viewing direction, wherein at least one objective which is arranged on the distal end of a shaft of the video endoscope and is movable relative to an image sensor about the longitudinal axis of the shaft and has at least one lateral viewing direction, wherein the viewing direction is changed-over from a first viewing direction to a second viewing direction on account of a viewing direction changeover command, and is further developed in that an orientation of the viewing direction is measured and at least one orientation marking which has been or is rotated in accordance with the measured orientation, is inserted in an image reproduction of the image data recorded by the image sensor.

The feature that at least one objective is arranged on the distal end of the shaft of the video endoscope and is movable relative to an image sensor about the longitudinal axis of the shaft and has at least one lateral viewing direction, is understood in the scope of the invention to comprise the case that an objective comprises a diverting element, for example a swing prism that provides a lateral view, and also the case that an objective which in a null position views in the 0° direction, can be tipped into a lateral view, as well as the case that a plurality of objectives are present with rigid polar angles, at least one of which has a lateral viewing direction. The movability of the objective about the longitudinal axis of the shaft can be attained in the scope of the invention either by a rotation of the objective about the longitudinal axis, or by tipping of an objective disposed on a platform, for example, which can be tipped in different directions, for example according to the document US 2006/0293565 A1. This also results in a rotation of the viewing direction about the longitudinal axis of the endoscope shaft.

Measuring the orientation of the viewing direction in space, or respectively relative to the orientation of the measuring sensor, and displaying orientation markings in the reproduced image, significantly improves orientation in the operative field for the surgeon. Even with complicated examinations or surgeries in which the endoscope frequently changes direction and rotates about the longitudinal axis of the shaft, the surgeon, who always has the image representation of the recorded images on the image display device, for example on a monitor, in view, has an indicator for the orientation at all times. This facilitates the hand-eye coordination for the surgeon.

The method according to the invention can be used both with video endoscopes with built-in image sensor and also with endoscopes with attached camera head, that is, with an external image sensor. Both cases are comprised in the scope of the invention under the term "video endoscope". Further comprised are stereo video endoscopes which comprise two image sensors and suitable objectives and possibly light guide systems.

If preferably, the at least one orientation marking is created so that the direction is displayed that corresponds to an azimuth angle difference between the instantaneously measured viewing direction of the objective and the orientation of the image sensor, then a representation is selected that is particularly simple to comprehend by the surgeon. In such cases, the surgeon typically holds the part of the endoscope comprising the image sensor in one hand, and in the other hand the part of the endoscope with which a rotation of the distal tip, for example of an objective head, or the objective in the shaft is moved. The orientation marking is therefore directly usable for coordinating the left hand and right hand of the surgeon. In cases in which adjusting the azimuth angle of the viewing direction and holding the endoscope is performed together with one hand, the same applies to coordinating the respective fingers of the other hand, which control the adjusting of the azimuth angle in viewing direction.

This type of representation is also particularly advantageous in a case, in which there is an objective that can be tipped in different directions, because in this case the surgeon has more degrees of freedom available for tip movements, and with this the orientation in space using the display of the instantaneously taken viewing direction is particularly helpful.

If a plurality of objectives are disposed at the distal end of the shaft which are aligned in different viewing directions, wherein the viewing direction is changed-over from a first viewing direction to a second viewing direction on account of a viewing direction changeover command, or if a swing prism is provided for this purpose, for example, then despite changing polar angles of the viewing directions, the orientation of the surgeon can be guaranteed, by preferably alternatively, or in addition, to the named orientation markings, advantageously providing that the at least one orientation marking or at least a second orientation marking is created and displayed such that it corresponds to one or more directions of possible viewing direction changeovers, particularly between the objectives or respectively the possible viewing directions.

With such an orientation marking, the surgeon is immediately informed in which direction the image will be changed when he changes over the viewing direction, that is, the polar angle of the viewing direction, for example, between 30° and 80°, or from 0° to 45°. Because the at least two objectives having different viewing directions typically lie in one plane with respect to the azimuth angle, which also applies for the case of using a swing prism or a swing mirror, the orientation marking which displays a direction of a possible viewing direction changeover also corresponds to an azimuth angle difference between the instantaneously measured viewing direction of the objective and the orientation of the image sensor.

If in an advantageous further development, an orientation marking which corresponds to a direction of a possible viewing direction changeover, is inserted only when the direction displayed by this orientation marking deviates from a likewise displayed orientation marking, which displays the azimuth angle between the objective and the image sensor, or that the orientation marking which displays the azimuth angle between the objective and the image sensor is displayed only when the direction displayed by this orientation marking deviates from a likewise displayed orientation marking which corresponds to the direction of a possible viewing direction changeover, then a manner of proceeding is attained which has a low redundancy because two orientation markings are not displayed pointing in the same direction. This keeps the viewing field on the image display device concise. In doing so it can be selected whether a possible viewing direction changeover or the general azimuthal orientation of the viewing direction is displayed by default.

It is further advantageous for the orientation of the surgeon in space if a further orientation marking is created and displayed such that it corresponds to a vertical parallel or antiparallel to the force of gravity. Such an orientation marking directly correlates with the orientation perception of the surgeon and enables him to perform immediate movements of the endoscope in the correct direction, and to record and correlate with it the appropriate image change.

Advantageously, the at least one orientation marking is permanently displayed, or displayed on request for a predetermined or pre-determinable duration, or on request up to a switch off command. With a permanent display, the orientation marking is continuously displayed; this facilitates orientation for the surgeon at any time. If this is not continuously necessary, one or more orientation markings can also be requested, either, which is very convenient for the surgeon, for a predetermined duration after which the marking is again removed, or up to a switch off command from the surgeon. It can also be provided, for example, to display a first orientation marking permanently, another upon request for a specific duration, and a third upon request up to a switch off command. These procedures can be meaningfully combined within the scope of the invention.

The named types of orientation markings can be displayed individually or in different combinations, simultaneously or alternating.

The object of the invention is also solved by a video endoscope system comprising a video endoscope, an image processing unit and an image display device, wherein the video endoscope has an image sensor and at least one objective which is arranged on the distal end of an endoscope shaft and is movable relative to an image sensor about the longitudinal axis of the shaft and having at least one lateral viewing direction, wherein the viewing direction can be changed-over from a first viewing direction to a second viewing direction on account of a viewing direction changeover command, which is further developed in that the video endoscope has at least one measuring device for measuring an orientation of the objective, and the image processing unit is designed to create at least one orientation marking and to insert the orientation marking which has been or is rotated in accordance with the measured orientation, into the image data recorded by the image sensor. This video endoscope system has all device components which are necessary and are designed, as described above, to measure the orientation of one or more image sensor components of a video endoscope, and to create and insert appropriate orientation markings into the image data processing.

In an advantageous further development, at least one measuring device is additionally provided to measure an orientation of the image sensor. Thereby the difference measurements of the orientation between the viewing directions of the objective, or the objectives, at the distal end of the shaft and the image sensor can be created.

Preferably, the image processing unit is designed to implement the previously described method according to the invention.

The measuring device is, or measuring devices are preferably implemented as gyroscope sensors, as inclination sensor/s, as acceleration sensor/s, as gravity sensor/s, as rotary encoder/s, and/or as rotary potentiometer/s.

The rotation of the viewing direction about the longitudinal axis of the shaft of the video endoscope occurs using mechanical means, or magnetic means, for example, a magnetic reach-through, similar to a manipulator in ultrahigh vacuum technology.

The objective addressed by the invention is finally solved by a software program product comprising program code means, the execution of which on a data processing device, particularly an image processing unit, implements the steps of the method according to the invention described above.

Finally, the object addressed by the invention is also solved by a software program product comprising program code means, the execution of which on a data processing device, particularly an image processing unit, which is particularly part of a previously described video endoscope system according to the invention, implements the steps of the previously described method according to the invention. The software program product can comprise a software and particularly also a data medium comprising the program code means.

The features, properties and advantages described previously in conjunction with the method according to the invention apply without restriction also to the further subject matters of the invention, namely the video endoscope system according to the invention and the software program product according to the invention having program code means, which have the same features, properties and advantages.

BRIEF DESCRIPTION OF THE DRAWINGS

The invention is described below, without restricting the general intent of the invention, based on exemplary embodiments in reference to the drawings, whereby we expressly refer to the drawings with regard to the disclosure of all details according to the invention that are not explained in greater detail in the text. They show:

FIG. 2 illustrates a schematic representation of images having orientation markings according to the invention, and FIG. 3 illustrates a further schematic representation of images having orientation markings according to the invention.

DETAILED DESCRIPTION

Figure 1:
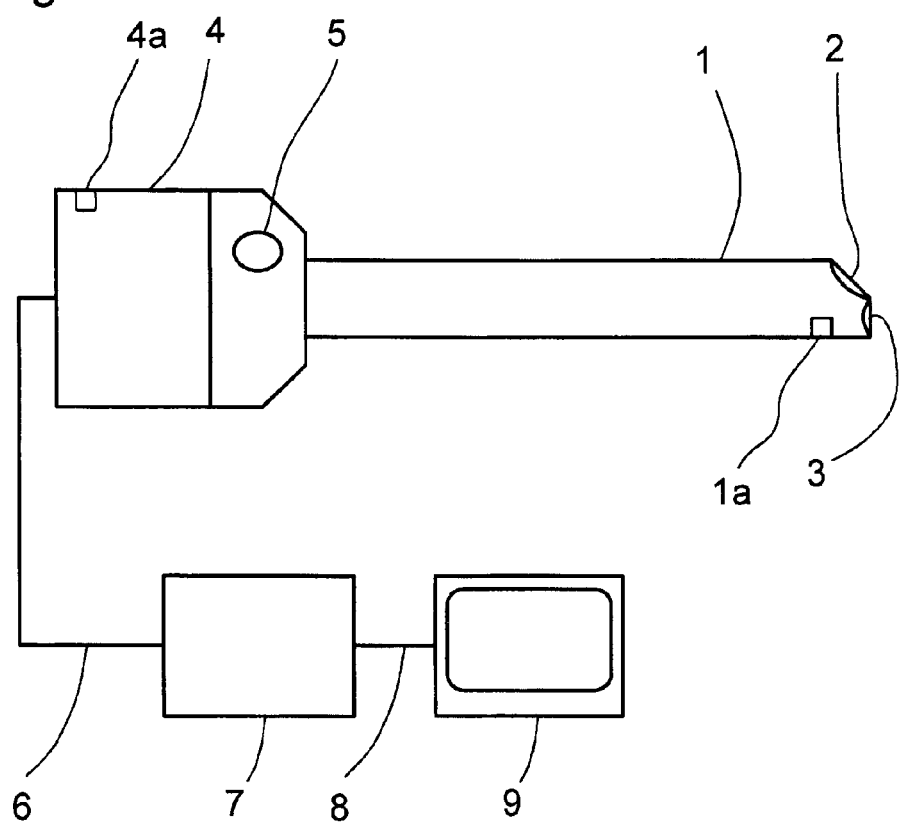
FIG. 1 illustrates a schematic representation of a video endoscope system according to the invention.

In the following figures, the same or similar types of elements or corresponding parts are provided with the same reference numbers so that a corresponding re-introduction can be omitted.

FIG. 1 schematically shows a video endoscope system according to the invention. A video endoscope has a longitudinally extended endoscope shaft 1, having a first objective lens 2 and a second objective lens 3 disposed at the distal tip thereof. The viewing angle of the second objective lens 3 is approximately in 0°-direction while the first objective lens 2 has a direction of view (DOV) of approximately 50°. The field of view, not shown, of the first objective lens 2 and the second objective lens 3 can overlap. The endoscope shaft 1 additionally has an orientation sensor 1a, by means of which the orientation of the endoscope shaft 1 and/or the objective lenses 2, 3 is measured. This can be a gyroscope sensor, an inclination sensor, an acceleration sensor or a gravity sensor. An implementation as a rotary encoder and/or as a rotary potentiometer for measuring the rotation of the objective lenses 2, 3 with the respect to the endoscope shaft 1, or the shaft 1 with respect to a handle 4, can also be used in the scope of the invention.

At the proximal end of the video endoscope, there is a handle 4 comprising a changeover button 5, with the actuation of which a changeover signal is generated upon which the viewing direction is changed over between the first objective lens 2 and the second objective lens 3. The handle 4 has an orientation sensor 4a, which also is developed as a gyroscope sensor, inclination sensor, acceleration sensor or gravity sensor for example.

The video endoscope is connected using a connection cable 6 to an image processing unit 7, and further via a connection cable to an image display device 9 upon which images are displayed that were recorded using the video endoscope through either the first objective lens 2 or the second objective lens 3, and were subsequently processed by the image processing unit 7.

FIG. 2 shows a first image 10 and a second image 11 before and after changing over between two viewing directions, that is, before and after the changeover of the polar angle of the viewing direction between two objective lenses 2, 3. Because the azimuth angle of the viewing directions with respect to the azimuth angle of the orientation of the image sensor is rotated by approximately 60°, the two images 10, 11 are also disposed offset by a corresponding angle with respect to each other.

In each case, a marking field 12 is inserted in the upper right corner, in which an orientation marking 13 appears that represents the relative orientation of the viewing direction, that is, the azimuth angle of the viewing direction to the orientation of the image sensor, which corresponds in the represented image 10, 11 in each case to the image orientation. Because the viewing direction change from the first image 10 to the second image 11 is accompanied by a change of the polar angle of the viewing direction, but not by a change of the azimuth angle of the viewing direction, the orientation marking 13 which is formed as an arrow, has the same direction before and after the change, because the two objectives 2, 3 are disposed in the same radial plane with respect to the longitudinal axis of the shaft 1 of the video endoscope. Alternatively according to the invention, an orientation marking 14 can be displayed instead, which displays a possible viewing direction change. In this case, the arrow in image 11 would be rotated by 180° with respect to the arrow shown.

FIG. 3 again shows a first image 10 and a second image 11, in which, as in FIG. 2, a marking field 12 is also shown in the upper right corner, and the already described orientation markings 13, shown in black, are displayed. In addition to this, with image 12 after the viewing direction changeover, a further orientation marking 14 is shown, which represents the next following direction changeover.

In this case, this means that with a further changeover the direction, to which the image 11 would change, that is, towards image 10, is opposite to the direction of the general orientation marking 13 with respect to the deviation from the longitudinal axis of the shaft 1. In order to indicate this, the orientation marking 14 is also inserted. Because in the image 10 the direction change with a changeover coincides with the general orientation which is represented by the orientation marking 13, the need to display a further orientation marking 14 for the direction change is obviated in image 10. Alternatively, in this case it is also possible to provide an orientation marking 14 in image 10, or at the marking field 12, for the changeover direction, which is superimposed on, or appended to the orientation marking 13. It can also be disposed in parallel to the orientation marking 13, or in another suitable manner.

Additionally, in the images 10 and 11, in each case in the upper left corner, a marking field 15 is represented having an orientation marking 16 formed in the style of a compass rose for the spatial direction, or respectively spatial orientation of the viewing direction of the endoscope. This orientation marking 16 facilitates the work for the surgeon, because it shows him in the image in which direction the force of gravity acting upon him acts. The compass rose can be aligned so that it shows the direction of gravity, or counter to the direction of gravity, vertically upward, or directly displays the direction of gravity downward.

An inclination sensor or a gravity sensor come into use in particular for measuring the direction of gravity, wherein additional sensors are used, which measure, for example, the azimuth angle between the viewing direction of the objectives and the image sensor, for correcting the measurement and for inserting these orientation markings into the displayed image.

All named characteristics, including those taken from the drawings alone, and individual characteristics, which are disclosed in combination with other characteristics, are considered individually and in combination as essential to the invention. Embodiments according to the invention can be fulfilled through individual characteristics or a combination of several characteristics.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE LIST

1 Endoscope shaft
1a Orientation sensor
2 First objective lens
3 Second objective lens
4 Handle
4a Orientation sensor
5 Changeover button
6 Connection cable
7 Image processing unit
8 Connection cable
9 Image reproduction device
10 First image
11 Second image
12 Marking field
13 Orientation marking
14 Orientation marking for changeover direction
15 Marking field
16 Orientation marking for spatial direction

What is claimed is:

1. A method for displaying an image acquired by an endoscope system, wherein the endoscope system comprises:
   an endoscope shaft extending along a longitudinal axis;
   optical elements and an image sensor arranged to the endoscope shaft, wherein the optical elements and the image sensor are configured to be controlled by a user to acquire a plurality of images in at least:
      a first view direction relative to the longitudinal axis of the endoscope shaft; and
      a second view direction relative to the longitudinal axis of the endoscope shaft, the second view direction being different from the first view direction,
      wherein the optical elements and the image sensor are configured to be controlled by the user to acquire an image in the second view direction after it is controlled by the user to acquire an image in the first view direction, and
   wherein the method comprises:
      controlling a display to display a current image acquired by the optical elements and the image sensor in the first view direction relative to the longitudinal axis of the endoscope shaft;
      controlling the display to display a first marking overlaid on the current image, the first marking indicating the first view direction; and
      controlling the display to display a second marking overlaid on the current image, the second marking indicating the second view direction relative to the longitudinal axis of the endoscope shaft in which the optical elements and the image sensor can be controlled by the user to acquire a future image in the second view direction after the acquisition of the current image.

2. The method according to claim 1,
   wherein the first marking corresponds to an azimuth angle difference between an instantaneously measured viewing direction of the optical elements and an orientation of the image sensor.

3. The method according to claim 2,
   wherein the first marking and the second marking are displayed permanently, or on request for a predetermined or pre-determinable duration, or on request up to a switch off command.

4. The method according to claim 1,
   wherein the second marking, which indicates the second view direction relative to the longitudinal axis of the endoscope shaft in which the optical elements and the image sensor can be controlled by the user to acquire a future image after the acquisition of the current image, is displayed only when the direction displayed by the second marking deviates from an orientation marking also displayed, which displays the azimuth angle between the optical elements.

5. The method according to claim 1, wherein the first marking and the second marking are displayed permanently, or on request for a predetermined or pre-determinable duration, or on request up to a switch off command.

6. An endoscope system comprising:
   an endoscope shaft extending along a longitudinal axis;
   optical elements and an image sensor arranged to the endoscope shaft, wherein the optical elements and the image sensor are configured to be controlled by a user to acquire a plurality of images in at least:
      a first view direction relative to the longitudinal axis of the endoscope shaft; and
      a second view direction relative to the longitudinal axis of the endoscope shaft, the second view direction being different from the first view direction,
      wherein the optical elements and the image sensor are configured to be controlled by the user to acquire an image in the second view direction after it is controlled by the user to acquire an image in the first view direction; and
   a processor configured to control a display to display:
      a current image acquired by the optical elements and the image sensor in the first view direction relative to the longitudinal axis of the endoscope shaft;
      a first marking overlaid on the current image, the first marking indicating the first view direction; and
      a second marking overlaid on the current image, the second marking indicating the second view direction relative to the longitudinal axis of the endoscope shaft in which the optical elements and the image sensor can be controlled by the user to acquire a future image in the second view direction after the acquisition of the current image.

7. The endoscope system according to claim 6, further comprising at least one measuring device for measuring an orientation of the optical elements and an orientation of the image sensor,
   wherein first marking corresponds to an azimuth angle difference between an instantaneously measured viewing direction of the optical elements and the orientation of the image sensor.

8. The endoscope system according to claim 7, wherein the measuring device comprises one of a gyroscope sensor, an inclination sensor, an acceleration sensor, a gravity sensor, a rotary encoder and a rotary potentiometer.

9. A computer-readable storage device storing instructions for displaying an image acquired by an endoscope system, wherein the endoscope system comprises:
   an endoscope shaft extending along a longitudinal axis;
   optical elements and an image sensor arranged to the endoscope shaft, wherein the optical elements and the image sensor are configured to be controlled by a user to acquire a plurality of images in at least:
      a first view direction relative to the longitudinal axis of the endoscope shaft; and
      a second view direction relative to the longitudinal axis of the endoscope shaft, the second view direction being different from the first view direction,
      wherein the optical elements and the image sensor are configured to be controlled by the user to acquire an image in the second view direction after it is controlled by the user to acquire an image in the first view direction, and
   wherein the instructions, upon execution by a processor, causes the processor to perform:
      controlling a display to display a current image acquired by the optical elements and the image sensor in the first view direction relative to the longitudinal axis of the endoscope shaft;
      controlling the display to display a first marking overlaid on the current image, the first marking indicating the first view direction; and
      controlling the display to display a second marking overlaid on the current image, the second marking indicating the second view direction relative to the longitudinal axis of the endoscope shaft in which the optical elements and the image sensor can be controlled by the user to acquire a future image in the second view direction after the acquisition of the current image.

* * * * *